United States Patent
Calancie et al.

(10) Patent No.: US 8,591,431 B2
(45) Date of Patent: Nov. 26, 2013

(54) SYSTEM AND METHODS FOR PERFORMING PEDICLE INTEGRITY ASSESSMENTS OF THE THORACIC SPINE

(75) Inventors: Blair Calancie, Manlius, NY (US);
James Gharib, San Diego, CA (US);
Allen Farquhar, San Diego, CA (US);
Doug Layman, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 709 days.

(21) Appl. No.: 11/994,411

(22) PCT Filed: Sep. 22, 2006

(86) PCT No.: PCT/US2006/037289
§ 371 (c)(1),
(2), (4) Date: Jan. 1, 2008

(87) PCT Pub. No.: WO2007/035925
PCT Pub. Date: Mar. 29, 2007

(65) Prior Publication Data
US 2008/0221473 A1    Sep. 11, 2008

Related U.S. Application Data

(60) Provisional application No. 60/719,886, filed on Sep. 22, 2005.

(51) Int. Cl.
*A61B 5/053* (2006.01)
(52) U.S. Cl.
USPC ........................................ 600/554; 600/546
(58) Field of Classification Search
USPC .................................. 600/546, 554
See application file for complete search history.

(56) References Cited

U.S. PATENT DOCUMENTS

| | | | |
|---|---|---|---|
| 2,736,002 | A | 2/1956 | Oriel |
| 3,785,368 | A | 1/1974 | McCarthy et al. |
| 4,545,374 | A | 10/1985 | Jacobson |
| 4,592,369 | A | 6/1986 | Davis et al. |
| 4,759,377 | A | 7/1988 | Dykstra |
| 4,962,766 | A | 10/1990 | Herzon |
| 4,964,411 | A | 10/1990 | Johnson et al. |

(Continued)

FOREIGN PATENT DOCUMENTS

| | | |
|---|---|---|
| DE | 29908259 | 8/1999 |
| EP | 0607688 | 7/1994 |

(Continued)

OTHER PUBLICATIONS

Lenke, L., et al. Triggered Electromyographic Threshold for Accuracy of Pedicle Screw Placement. Spine 1995; 20 (14): 1585-1591.

(Continued)

*Primary Examiner* — Joseph Stoklosa
(74) *Attorney, Agent, or Firm* — Jonathan Spangler; Rory Schermerhorn; Heather Prado

(57) ABSTRACT

The present invention includes a system and methods aimed at surgery, and more particularly to a system and methods for monitoring nervous tissue to assess the integrity of a pedicle wall during or after pilot hole formation and before, during, or after screw implantation, particularly in the thoracic spine. The system also performs other neurophysiologic assessments including, but not necessarily limited to, neuromuscular pathway status, nerve proximity detection, nerve pathology monitoring, and spinal cord health monitoring.

25 Claims, 10 Drawing Sheets

(56) References Cited

U.S. PATENT DOCUMENTS

| | | | |
|---|---|---|---|
| 5,196,015 A | 3/1993 | Neubardt | |
| 5,284,153 A | 2/1994 | Raymond et al. | |
| 5,284,154 A | 2/1994 | Raymond et al. | |
| 5,375,067 A | 12/1994 | Berchin | |
| 5,474,558 A | 12/1995 | Neubardt | |
| 5,480,440 A | 1/1996 | Kambin | |
| 5,775,331 A | 7/1998 | Raymond et al. | |
| 5,779,642 A | 7/1998 | Nightengale | |
| 5,806,522 A | 9/1998 | Katims | |
| 5,830,151 A | 11/1998 | Hadzic et al. | |
| 5,928,158 A | 7/1999 | Aristides | |
| 5,935,131 A | 8/1999 | Bonutti | |
| 6,027,456 A | 2/2000 | Feler et al. | |
| 6,038,477 A | 3/2000 | Kayyali | |
| 6,104,957 A | 8/2000 | Alo et al. | |
| 6,104,960 A | 8/2000 | Duysens et al. | |
| 6,119,068 A | 9/2000 | Kannonji | |
| 6,128,576 A | 10/2000 | Nishimoto | |
| 6,138,681 A | 10/2000 | Chen et al. | |
| 6,181,961 B1 | 1/2001 | Prass et al. | |
| 6,266,558 B1 | 7/2001 | Gozani et al. | |
| 6,306,100 B1 | 10/2001 | Prass et al. | |
| 6,334,068 B1 | 12/2001 | Hacker | |
| 6,466,817 B1 | 10/2002 | Kaula et al. | |
| 6,579,244 B2 | 6/2003 | Goodwin | |
| 6,719,692 B2 | 4/2004 | Kleffner et al. | |
| 6,796,985 B2 | 9/2004 | Bolger et al. | |
| 6,819,956 B2 | 11/2004 | DiLorenzo | |
| 6,849,047 B2 | 2/2005 | Goodwin | |
| 6,855,105 B2 | 2/2005 | Jackson, III et al. | |
| 6,929,606 B2 | 8/2005 | Ritland | |
| 7,089,059 B1 | 8/2006 | Pless | |
| 7,657,308 B2 * | 2/2010 | Miles et al. | 600/546 |
| 7,664,544 B2 * | 2/2010 | Miles et al. | 600/546 |
| 2004/0225228 A1 * | 11/2004 | Ferree | 600/554 |
| 2005/0033380 A1 | 2/2005 | Tanner et al. | |
| 2005/0192575 A1 | 9/2005 | Pacheco | |
| 2008/0064976 A1 | 3/2008 | Kelleher et al. | |
| 2008/0064977 A1 | 3/2008 | Kelleher et al. | |

FOREIGN PATENT DOCUMENTS

| | | | |
|---|---|---|---|
| EP | 1146816 | | 10/2001 |
| FR | 2795624 | | 1/2001 |
| WO | WO 03/037170 | * | 5/2003 |

OTHER PUBLICATIONS

"Brackman II EMG System," Medical Electronics, 1994, 4 pages.
"Neurovision SE Nerve Locator / Monitor," RLN Systems, Inc. Operator's Manual, 1999, 22 pages.
"The Brackman II EMG Monitoring System," Medical Electronics Co. Operator's Manual Version 1.1, 1995, 50 pages.
"The Nicolet Viking IV," Nicolet Biomedical Products, 1999, 6 pages.
Anderson, D. G., et al. Pedicle Screws with High Electrical Resistance: A Potential Source of Error with Stimulus-Evoked EMG. Spine 2002; 27(14): 1577-1581.
Bose, B., et al. Neurophysiologic Monitoring of Spinal Nerve Root Function During Instrumented Posterior Lumbar Spine Surgery. Spine 2002; 27(13): 1444-1450.
Calancie, B. et al. Stimulus-Evoked EMG Monitoring During Transpedicular Lumbosacral Spine Instrumentation. Spine 1994; 19(24): 2780-2876.
Clements, D., et al. Evoked and Spontaneous Electromyography to Evaluate Lumbosacral Pedicle Screw Placement. Spine 1996; 21(5): 600-604.
Danesh-Clough, T., et al. The Use of Evoked EMG in Detecting Misplaced Thoracolumbar Pedicle Screws. Spine 2001; 26(12): 1313-1316.
Darden, B., et al. A Comparison of Impedance and Electromyogram Measurements in Detecting the Presence of Pedicle Wall Breakthrough. Spine 1998; 23(2): 256-262.
Ebraheim, N. Anatomic Relations Between the Lumbar Pedicle and the Adjacent Neural Structures. Spine 1997; 22(20): 2338-2341.
Ford, et al. Electrical Characteristics of Peripheral Nerve Stimulators: Implications for Nerve Localization. Reg Anesth 1984: 9: 73-77.
Glassman, S., et al. A Prospective Analysis of Intraoperative Electromyographic Monitoring of Pedicle Screw Placement With Computed Tomographic Scan Confirmation. Spine 1995; 20(12): 1375-1379.
Greenblatt, et al. Needle Nerve Stimulator-Locator: Nerve Blocks with a New Instrument for Locating Nerves. Anesth & Analg 1962; 41(5): 599-602.
Haig. Point of View. Spine 2002; 27(24): 2819.
Haig, et al. The Relation Among Spinal Geometry on MRI, Paraspinal Electromyographic Abnormalities, and Age in Persons Referred for Electrodiagnostic testing of Low Back Symptoms. Spine 2002; 27(17) 1918-1925.
Holland, N, et al. Higher Electrical Stimulus Intensities are Required to Activate Chronically Compressed Nerve Roots: Implications for Intraoperative Electromyographic Pedicle Screw Testing. Spine 1998; 23(2): 224-227.
Holland, N., et al. Intraoperative Electromyography During Thoracolumbar Spinal Surgery. Spine 1998; 23(17): 1915-1922.
Journee, H., et al. System for Intra-Operative Monitoring of the Cortical Integrity of the Pedicle During Screw Placement in Lowback Surgery: Design and Clinical Results. Sensory and Neuromuscular Diagnostic Instrumentation and Data Analysis, 18th Annual International Conference on Engineering in Medicine and Biology Society, Oct. 1996; 1(31): 144-145.
Maguire, J., et al. Evaluation of Intrapedicular Screw Position Using Intraoperative Evoked Electromyography. Spine 1995; 20(9): 1068-1074.
Martin, et al. Initiation of Erection and Semen Release by Rectal Probe Electrostimulation (RPE), J of Urol 1983; 129: 637-642.
Minahan, R., et al. The Effect of Neuromuscular Blockade on Pedicle Screw Stimulation Thresholds. Spine 2000; 25(19); 2526-2530.
Pither, et al. The Use of Peripheral Nerve Stimulators for Regional Anesthesia: Review of Experimental Characteristics, Technique, and Clinical Applications. Regional Anesth 1985; 10: 49-58.
Raj, et al. Infraclavicular Brachial Plexus Block: A New Approach. Anesth and Analg 1973; 52(6): 897-904.
Raj, et al. The Use of Peripheral Nerve Stimulators for Regional Anesthesia, Clin Issues in Regional Anesth 1985; 1(4): 1-6.
Raj, et al. Use of the Nerve Stimulator for Peripheral Blocks. Regional Anesth 1980; 14-21.
Raymond, et al. The Nerve Seeker: A System for Automated Nerve Localization. Regional Anesth 1992; 17(3): 151-162.
Shafik. Cavernous Nerve Stimulation Through an Extrapelvic Subpubic Approach: Role in Penile Erection. Eur Urol 1994; 26: 98-102.
Toleikis, J., et al. The Usefulness of Electrical Stimulation for Assessing Pedicle Screw Requirements. Journal of Spinal Disorders 2000; 13(4): 283-289.
Moed, et al. Insertion of an Iliosacral Implant in an Animal Model. J of Bone and Joint Surg 1999; 81A(11): 1529-1537.
"NIM-Response, so advanced . . . yet so simple." XoMed, Inc. 1999, 12 pages.
Moed, et al. Intraoperative Monitoring with Stimulus-Evoked Electromyography During Placement of Iliosacral Screws. J Bone and Joint Surg 1998; 81A(4): 537-546.
"New data analyzer combines the functions of six instruments in one unit." News Release, Nov. 11, 1987, 3 pages.
"NuVasive's spine surgery system cleared in the US." Pharm & Medical Industry Week, Dec. 10, 2001, 1 page.
"Risk capital funds." Innovation 1990; 172: 3 pages.
Welch, et. al. Evaluation With Evoked and Spontaneous Electromyography During Lumbar Instrumentation: A Prospective Study. Journal of Neurosurgery 1997; 87: 397-402.
Zouridakis, et al., A Concise Guide to Intraoperative Monitoring, Ch. 1, CRC Press (2001).
"Electromyography System," International Search Report, International Patent Application No. PCT/US00/32329, Apr. 27, 2001, 9 pages.

(56) References Cited

OTHER PUBLICATIONS

"Nerve Proximity and Status Detection System and Method," International Search Report from International Application No. PCT/US01/18606, Oct. 18, 2001, 6 pages.

"Relative Nerve Movement and Status Detection System and Method," International Search Report from International application No. PCT/US01/18579, Jan. 15, 2002, 6 pages.

"System and Methods for Determining Nerve Proximity, Direction, and Pathology During Surgery," International Search Report, International Patent No. PCT/US02/22247, Mar. 27, 2003, 4 pages.

"System and Methods for Determining Nerve Direction to a Surgical Instrument," International Search Report from International Application No. PCT/US03/02056, Aug. 12, 2003, 5 pages.

"Systems and Methods for Performing Percutaneous Pedicle Integrity Assessments," International Search Report, International Patent Application No. PCT/US/02/35047, Aug. 11, 2003, 5 pages.

"Systems and Methods for Performing Surgery Procedures and Assessments," International Search Report, International Application No. PCT/US02/30617, Jun. 5, 2003, 4 pages.

"System and Methods for Performing Neurophysiologic Assessments During Spine Surgery," International Search Report from International Application No. PCT/US06/03966, Oct. 23, 2006, 5 pages.

"Multi-Channel Stimulation Threshold Detection Algorithm for Use in Neurophysiology Monitoring," International Search Report from International Application No. PCT/US06/37013, Mar. 19, 2007, 10 pages.

"Systems and Methods for Performing Dynamic Pedicle Integrity Assessments," International Search Report, International application No. PCT/US04/025550, Jun. 3, 2005, 3 pages.

* cited by examiner

Single Pulse Stimulation Signal

Multipulse Stimulation Signal

… … …

SYSTEM AND METHODS FOR PERFORMING PEDICLE INTEGRITY ASSESSMENTS OF THE THORACIC SPINE

CROSS-REFERENCE TO RELATED APPLICATIONS

This application is International Patent application claiming the benefit of priority from commonly owned and co-pending U.S. Provisional Patent Application Ser. No. 60/719,886, entitled "System and Methods For Performing Pedicle Integrity Assessments of the Thoracic and/or Cervical Spine," and filed on Sep. 22, 2005.

BACKGROUND

1. Field

The present invention relates generally to a system and methods aimed at surgery, and more particularly to a system and methods for monitoring nervous tissue to assess the integrity of a pedicle wall during or after pilot hole formation and before, during, or after screw implantation, particularly in the thoracic spine.

2. Background

Pedicle fixation is one of the most common methods used to fix vertebra relative to each other in the rapidly expanding discipline of spinal fusion. Pedicle fixation generally involves the implantation of a pedicle screw in each of at least two adjacent vertebra and securing of a rod thereafter to each pedicle screw, eliminating movement between the vertebra. By way of example, FIG. 1 depicts a cross sectional view of a vertebra 1 with attached pedicle screw 7. The pedicle 2 is essentially a narrow bone bridge connecting the vertebral body 3 with the posterior elements 4 of the vertebra 1. When properly positioned the pedicle screw 7 is anchored through the center of the pedicle and into the vertebral body 3 for maximum purchase.

Because of the extreme closeness of neural tissue all around the pedicle, the risk of neurological impairment is a paramount concern during pedicle screw fixation, as it is in all procedures performed in close proximity to neural tissue. The spinal canal 5, which houses the spinal cord in the cervical and thoracic spine, and nerve roots in the lumbar spine, lies just medial to the pedicle, and exiting nerve roots leave the spinal canal 5 directly above and below the pedicle 2. There is thus little room for error when implanting pedicle screws and any such error may have dire consequences. If the pedicle (or more specifically, the cortex of the medial wall, lateral wall, superior wall and/or inferior wall) is breached, cracked, or otherwise compromised, the patient may experience neurologic deficit due to unwanted contact between the pedicle screw (or other instruments used during screw placement or pilot hole formation) and delicate neural structures such as the spinal cord or nerve roots. The neurologic deficit may range from a slight loss of sensation to paralysis. Even absent neurologic impairment, an improperly placed pedicle screw still oftentimes necessitates revision surgery, which is disadvantageously painful for the patient and costly, both in terms of recovery time and hospitalization.

It should be appreciated that the "thoracic" region, as used herein and indicated in FIG. 2, includes the thoracic vertebra as well as the first lumbar vertebra L1 (also termed the "thoracolumbar" region). The "lumbar" spine, as used herein, begins at L2 and includes the sacral vertebra (also termed "lumbosacral" region). This is to account for the fact that the spinal cord actually ends at L1 and thus cord stimulation at L1 is a factor.

To combat the risk of neurological impairment during pedicle screw fixation in the lumbar spine, many surgeons rely on neurophysiology monitoring to monitor nerves and help avoid, or at least alert them to, a pedicle breach. Pedicle integrity assessments, sometimes called screw tests, capitalize on the insulating characteristics of bone and the conductivity of the neural structures. That is, if the pedicle is breached, a pulse of electrical current applied to the pedicle screw and/or the pilot hole (prior to screw introduction) will cause the nearby nerve root to depolarize and various muscle groups innervated by the nerve will contract. If the pedicle wall has not been breached, the insulating nature of the pedicle will prevent the stimulation signal from depolarizing the given nerve roots such that the associated muscle groups will not twitch. EMG systems may be used to augment the ability to detect muscle response to the stimulus.

Screw testing may greatly reduce the risk associated with implanting a pedicle screw in the lumbar region. This is not necessarily so in the thoracic region because the presence of the spinal cord in the spinal canal (as opposed to only nerve roots in the spinal canal of the lumbar region) complicates the screw test. While a screw test in the thoracic region may reveal lateral, superior, and/or inferior pedicle breaches, which would result in stimulation of a nerve root, a medial breach may go undetected because the same stimulation signal may not produce a measurable response when communicating with the spinal cord. With the presence of the spinal cord and the smaller size of the pedicle structure in the thoracic region, the ability to accurately test pedicle integrity may be every bit as beneficial, if not more so, as it has proven to be in the lumbar region. Although not a traditional concern in cervical screw placement (cervical screws generally placed in lateral mass vs. the pedicle), pedicle screw testing my be of benefit if pedicle-based fixation in the cervical spine becomes viable based on technical advances in screw technology.

Based on the foregoing, a need exists to better assess the integrity of pedicles during pedicle fixation in the presence of the spinal cord, particularly in the thoracic region of the spine. The invention described herein is aimed at addressing this need.

SUMMARY OF THE INVENTION

The present invention includes a system and related methods for performing neurophysiologic assessments performing pedicle integrity assessments (screw tests) of the thoracic and cervical spine.

According to a broad aspect, the present invention includes a neuromonitoring system, comprising a control unit, a stimulator, and a sensor and method for using the system for bone integrity testing. The control unit is configured to direct the stimulator to deliver stimulation signals of multiple electrical pulses, receive and process neuromuscular responses detected by the sensor, and identify a relationship between the neuromuscular response and the stimulation signal to assess whether a portion of vertebral bone has been breached or is close to being breached due to the implantation of a bone screw or formation and preparation of a pilot hole.

In one embodiment, the relationship identified between the neuromuscular response and the stimulation signal is the lowest (threshold) stimulation that is necessary to evoke a significant neuromuscular response. A significant neuromuscular response is a response of a predetermined magnitude.

In one embodiment, the control unit is configured to display one of graphical, alpha-numeric, and color based indicia to communicate the stimulation results to the user in a simple fashion. The control unit may also include a graphical user interface to receive user instructions.

In one embodiment, the stimulation signal comprises several electrical pulses of a constant current. The stimulation signal may include a train of pulses ranging in number from 2 to 8. The pulses may be separated by an interpulse gap ranging from 1 ms to 10 ms and the pulse widths may range from 50 µs to 400 µs. The use of the multipulse stimulation signal may improve that reproducibility of activating the spinal cord with a particular degree of communication and thus result in a more reliable stimulation threshold determination for thoracic and cervical screw testing.

In one embodiment, the control unit executes an algorithm to automatically adjust the stimulation current until the stimulation threshold, $I_{thresh}$, is found. The algorithm may utilize a bracketing method and bisection method to quickly determine $I_{thresh}$. The bracketing method proceeds by beginning stimulation at a predetermined minimum current and exponentially doubling the current with each stimulation thereafter until a the upper boundary of the bracket is found. The upper boundary of the bracket is the first stimulation current that evokes a significant neuromuscular response. The bisection method proceeds by stimulating with a current at the midpoint of the bracket and shrinking the bracket to either the upper half or lower half. If the stimulation current at the midpoint evokes a significant response, the bracket shrinks to the upper half. If the stimulation current does not evoke a significant response, the bracket shrinks to the lower half. The bisection process continues until the bracket has shrunken to predetermined range. $I_{thresh}$ may be selected as any value within the final bracket. After $I_{thresh}$ has been found, the algorithm may continue to verify the result by stimulating at the upper and lower boundaries of the final bracket. The algorithm may determine $I_{thresh}$ one time and then stop, or, the algorithm may continue to update the result until user intervention occurs.

In one embodiment, the sensors included with the system are EMG electrodes. The EMG electrodes detect the electric voltage associated with a muscle contraction. Preferably, the system uses 8 EMG electrodes to monitor 8 different myotomes during nerve monitoring.

In a further embodiment, the control unit communicates with a surgical instrument to transmit the stimulation signal to the nervous tissue. The surgical instrument has at least one stimulation electrode region linked to the control unit for transmitting the stimulation signal. The surgical instrument may be directly linked to the stimulator or the surgical instrument may be linked to the stimulator by a coupling device. The surgical instrument may be configured to deliver stimulation signal while in use forming or preparing a pedicle.

In one embodiment, the control unit may be further configured to assess other neurophysiologic conditions. The control unit may be configured to assess one of pedicle integrity of the lumbar spine, nerve proximity, nerve pathology, neuromuscular pathway status, and spinal cord health.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

Figure 1:
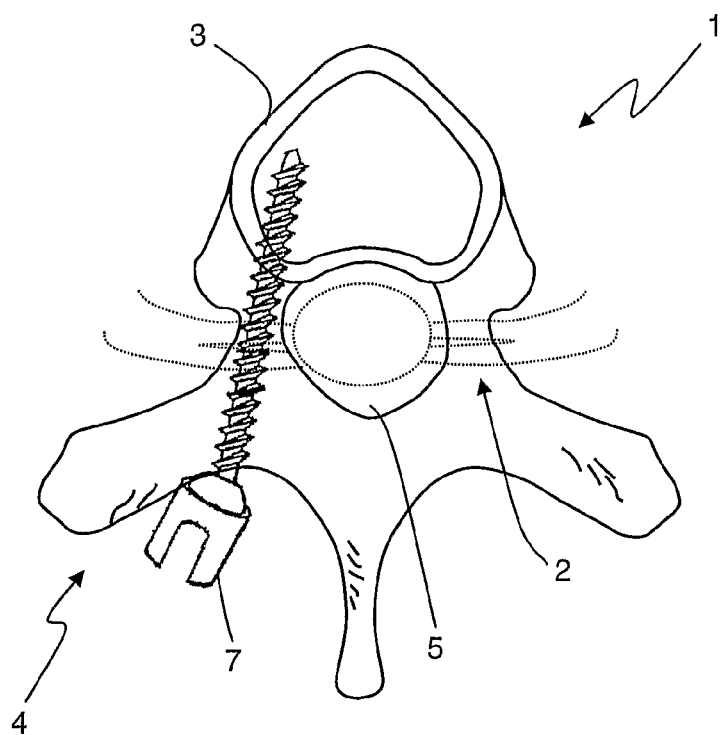
FIG. 1 is a cross sectional view illustrating the anatomy of a vertebra and the proper placement of a pedicle screw.
Figure 2:
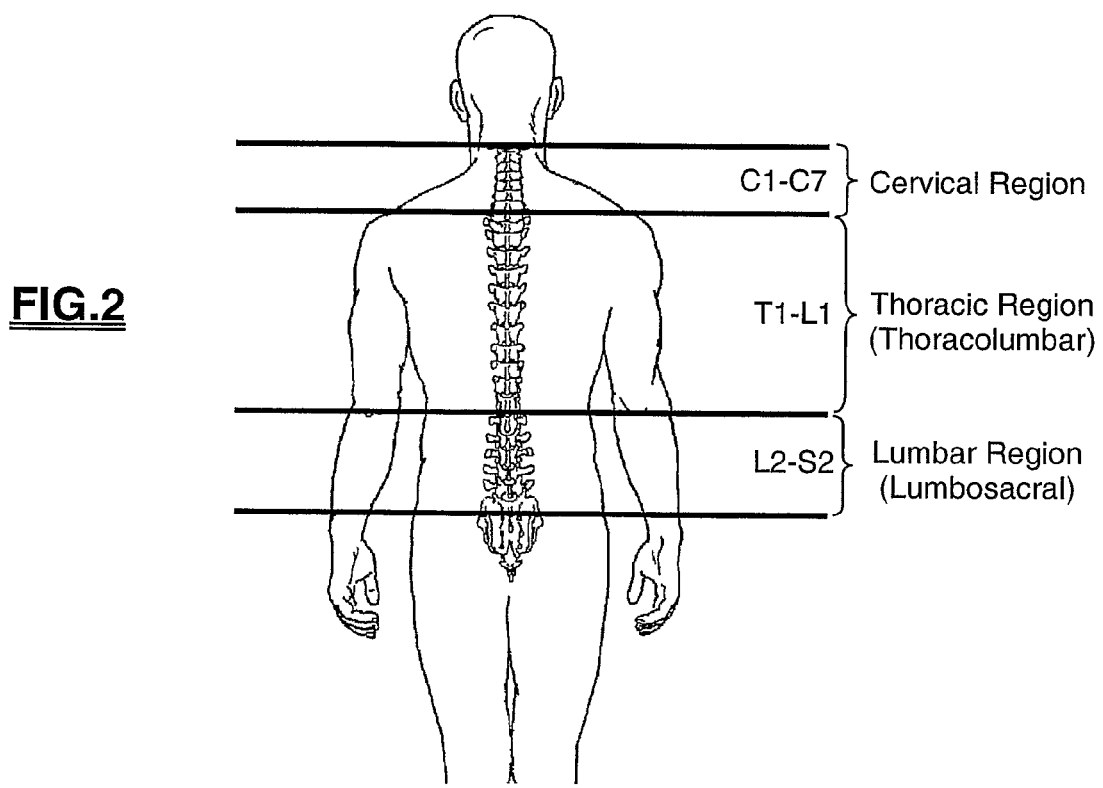
FIG. 2 is a back view demonstrating the different regions of the human spinal column for the purposes of this invention.
Figure 3:
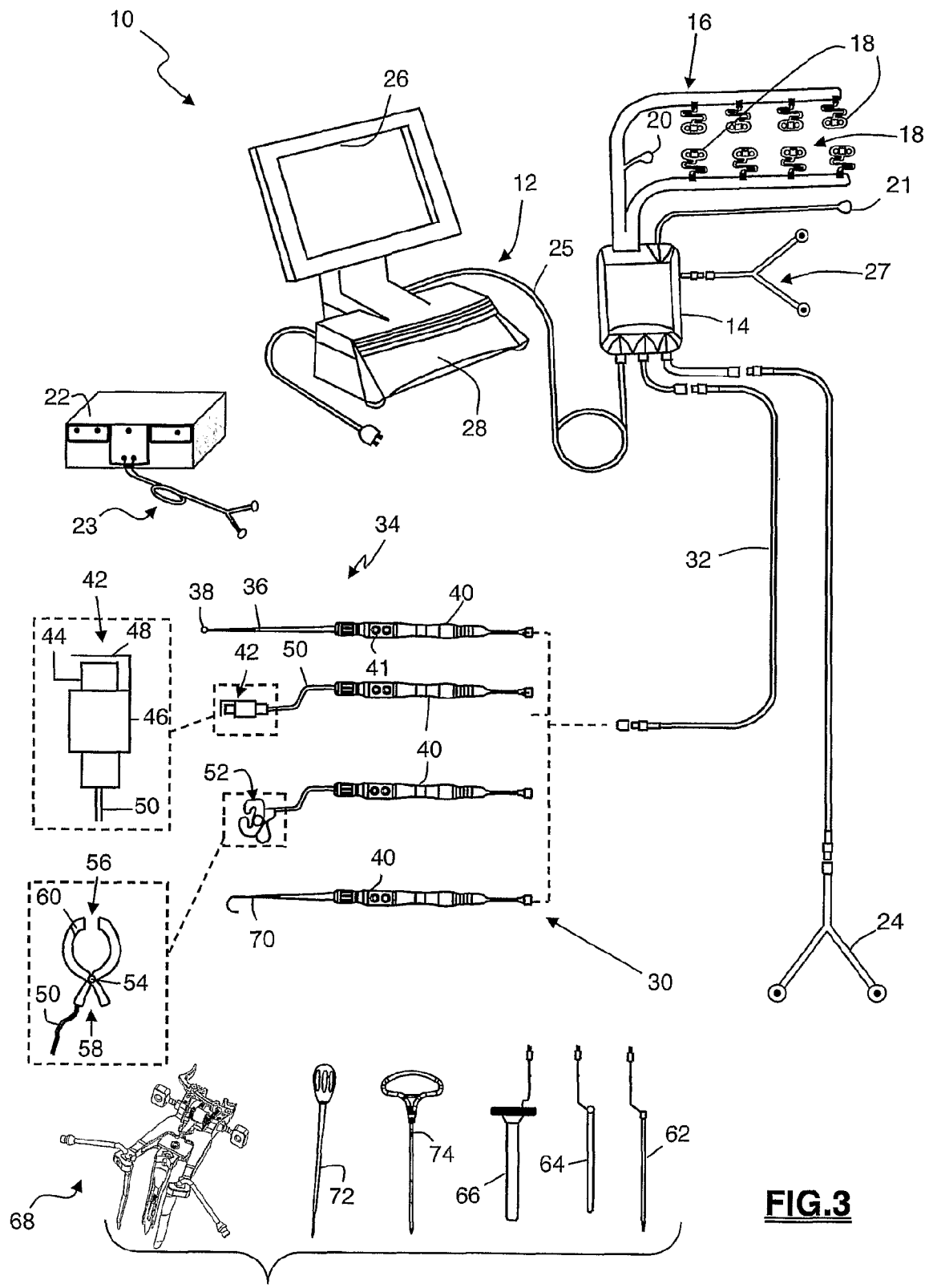
FIG. 3 is a perspective view of an exemplary neuromonitoring system 10 capable of performing neurophysiologic assessments such as for example, detecting pedicle breaches, nerve proximity (detection), nerve pathology, neuromuscular pathway status, and spinal cord health.

The system described herein is directed towards performing pedicle integrity assessments and particularly pedicle integrity assessments in the thoracic and/or cervical spine. Other neurophysiologic assessments may also be performed before, during, and/or after surgery. FIG. 3 illustrates, by way of example only, a neuromonitoring system 10 capable of carrying out neurophysiologic assessment functions including, but not necessarily limited to, Twitch Test (neuromuscular pathway assessment), Screw Test (pedicle integrity testing), Detection (nerve proximity testing during surgical access), Nerve Retractor (nerve pathology monitoring), MEP (Motor Evoked Potential spinal cord monitoring), and SSEP (Somatosensory Evoked Potential spinal cord monitoring). It is expressly noted that, although described herein largely in terms of use in spinal surgery, the neuromonitoring system 10 and related methods of the present invention are suitable for use in any number of additional surgical procedures where neurological impairment is a concern.

The neuromonitoring system 10 includes a control unit 12, a patient module 14, an EMG harness 16, including eight pairs of EMG electrodes 18 and a return electrode 21 coupled to the patient module 14, and one or more of a host of surgical accessories 30 capable of being coupled to the patient module via accessory cables 32. Additional components may include, a pair of peripheral nerve stimulation (PNS) electrodes (one positive and one negative) 24 also coupled to the patient module 14 and an MEP stimulator 22 including a pair of stimulation electrodes 23. The surgical accessories 30 may include, but are not necessarily limited to, devices for performing pedicle screw tests (such as a screw test probe 34 and electric coupling devices 42 or 52), surgical access components (such as a K-wire 62, one or more dilating cannula 64, a working cannula 66, and tissue retractor assembly 68), and neural pathology monitoring devices (such as a nerve root retractor 70).

Figure 4:
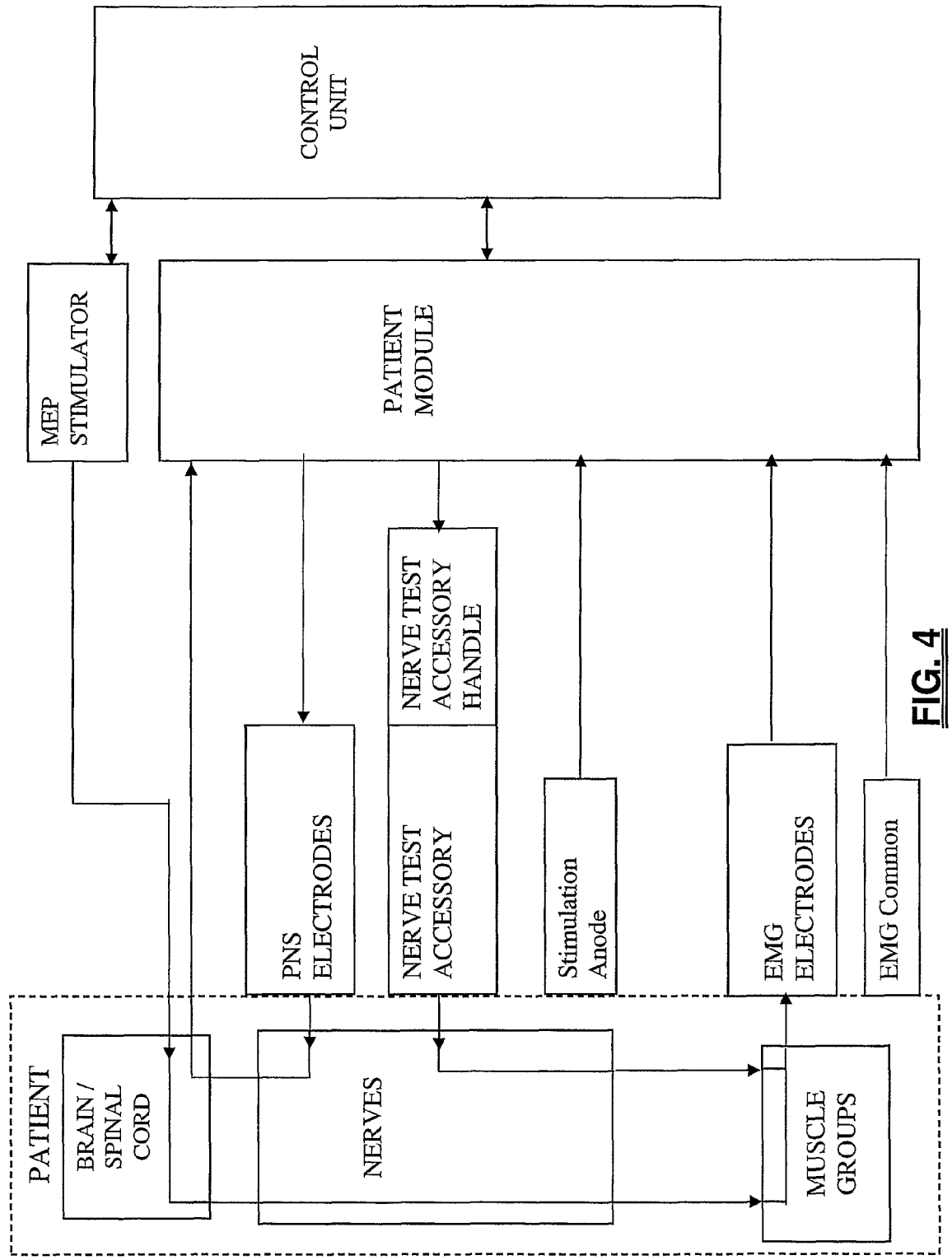
FIG. 4 is a block diagram of the neuromonitoring system 10 shown in FIG. 3.

A block diagram of the neuromonitoring system 10 is shown in FIG. 4, the operation of which is readily apparent in view of the following description. The control unit 12 includes a touch screen display 26 and a base 28, which collectively contain the essential processing capabilities for controlling the neuromonitoring system 10. The touch screen display 26 is preferably equipped with a graphical user interface (GUI) capable of communicating information to the user and receiving instructions from the user. The base 28 contains computer hardware and software that commands the stimulation sources, receives digitized signals and other information from the patient module 14, processes the EMG responses, displays the processed data to the operator via the display 26, and enables network connectivity. The primary functions of the software within the control unit 12 include receiving user commands via the touch screen display 26, activating stimulation in the requested mode (neuromuscular pathway assessment, screw test, nerve proximity, nerve direction, nerve pathology), processing signal data according to defined algorithms (described below), displaying received parameters and processed data, monitoring system status, and communicating with a remote client.

The patient module 14 is connected via a data cable 25 to the control unit 12, and contains the electrical connections to all electrodes, signal conditioning circuitry, stimulator drive and steering circuitry, and a digital communications interface to the control unit 12. In use, the control unit 12 is situated outside but close to the surgical field (such as on a cart adjacent the operating table) such that the display 26 is directed towards the surgeon for easy visualization. The patient module 14 should be located between the patient's legs, or may be affixed to the end of the operating table at mid-leg level using a bedrail clamp. The position selected should be such that the EMG leads can reach their farthest desired location without tension during the surgical procedure. MEP stimulator 22 is connected to the control unit 12 via a data cable, or preferably a wireless connection may be employed. MEP stimulator 22 includes a high voltage transformer and signal conditioning circuitry (not shown), for delivering the high voltage output stimulation signal required for MEP. MEP stimulator is preferably positioned near the control unit 12 and may be fashioned with a mount or hook and hung from the surgical table, an IV pole near the patient's head, or other equipment positioned near the patient.

The information displayed to the user on the display 26 may include, but is not necessarily limited to, alpha-numeric and/or graphical information regarding any of the requested modes (e.g., MEP, SSEP, Twitch Test, Free-Run EMG, Screw Test (Basic, Difference, Dynamic), Detection, and Nerve Retractor), myotome/EMG levels, stimulation levels, etc. . . . In one embodiment, set forth by way of example only, this information may include at least some of the following components (depending on the active mode) as set forth in Table 1:

TABLE 1

| Screen Component | Description |
| --- | --- |
| Spine Image | An image of the human body/skeleton showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Menu | A drop down navigation component for toggling between functions. |
| Display Area | Shows procedure-specific information including stimulation results. |
| Color Indication | Enhances stimulation results with a color display of green, yellow, or red corresponding to the relative safety level determined by the system. |
| Mode Indicator | Graphics and/or name to indicate the currently active mode (MEP, SSEP, Twitch Test, Free-Run EMG, Basic Screw Test, Dynamic Screw Test, Difference Screw Test, Detection, Nerve Retractor). In an alternate embodiment, Graphics and/or name may also be displayed to indicate the instrument in use, such as the dilator, K-wire, retractor blades, screw test instruments, and associated size information, if applicable, of the cannula, with the numeric size. If no instrument is in use, then no indicator is displayed. |
| Stimulation Bar | A graphical stimulation indicator depicting the present stimulation status (i.e. on or off and stimulation current level) |
| Sequence Bar | Shows the last seven stimulation results and provides for annotation of results. |
| EMG waveforms | EMG waveforms may be optionally displayed on screen along with the stimulation results. |

TABLE 1-continued

| Screen Component | Description |
| --- | --- |
| Setup Options | User selectable markers allow for the manual setting and/or changing of various parameters utilized by the system 10 to undertake nerve monitoring |

Figure 6:
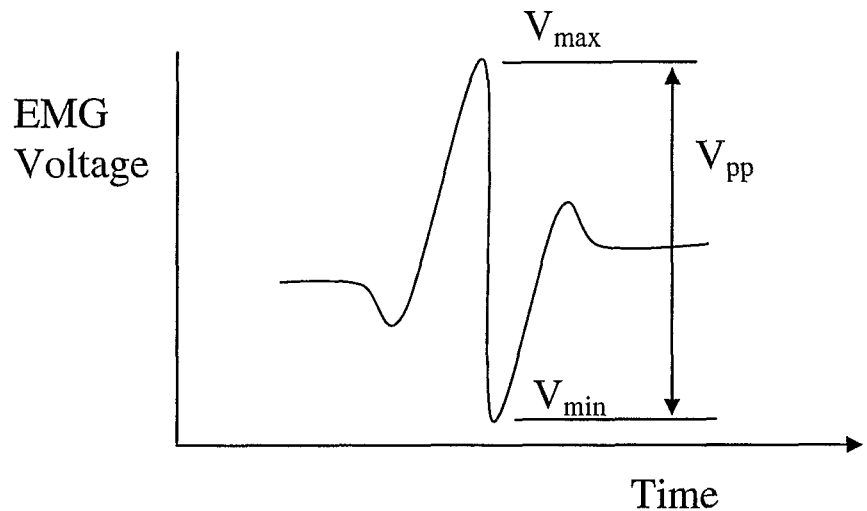
FIG. 6 is a graph illustrating an exemplary EMG response to the stimulus of FIG. 9 or 10.

Much of the neuromonitoring functionality of the neuromonitoring system 10 is based on assessing the evoked response of the various muscles myotomes monitored by the system 10 in relation to a stimulation signal transmitted by the system 10. The EMG responses, illustrated by way of example in FIG. 6, provide a quantitative measure of the nerve depolarization caused by the electrical stimulus. In one embodiment, EMG response monitoring is accomplished via 8 pairs EMG electrodes 18 (placed on the skin over the muscle groups to be monitored), a common electrode 20 providing a ground reference to pre-amplifiers in the patient module 14, and an anode electrode 21 providing a return path for the stimulation current. An exemplary EMG electrode for use with the system 10 is the dual surface electrode which is shown and described in detail in the commonly owned and co-pending U.S. patent application Ser. No. 11/048,404, entitled "Improved Electrode System and Related Methods," filed on Jan. 31, 2005, which is expressly incorporated by reference into this disclosure as if set forth in its entirety herein. It should be appreciated however, that any of a variety of known electrodes can be employed, including but not limited to surface pad electrodes and needle electrodes. It should also be appreciated that EMG electrode placement depends on a multitude of factors, including for example, the spinal cord level and particular nerves at risk and user preference, among others. In one embodiment (set forth by way of example only), the preferred EMG configuration is described for Lumbar surgery in Table 2, Thoracic surgery in Table 3, and Cervical surgery in Table 4 below. Alternatively, larger electrodes may be used and placed over several muscle groups at to increase coverage.

TABLE 2

| Lumbar | | | | |
| --- | --- | --- | --- | --- |
| Color | Channel | Myotome | Nerve | Spinal Level |
| Red | Right 1 | Right Vastus Medialis | Femoral | L2, L3, L4 |
| Orange | Right 2 | Right Tibialis Anterior | Common Peroneal | L4, L5 |
| Yellow | Right 3 | Right Biceps Femoris | Sciatic | L5, S1, S2 |
| Green | Right 4 | Right Medial Gastroc. | Post Tibial | S1, S2 |
| Blue | Left 1 | Left Vastus Medialis | Femoral | L2, L3, L4 |
| Violet | Left 2 | Left Tibialis Anterior | Common Peroneal | L4, L5 |
| Gray | Left 3 | Left Biceps Femoris | Sciatic | L5, S1, S2 |
| White | Left 4 | Left Medial Gastroc. | Post Tibial | S1, S2 |

TABLE 3

| Thoracolumbar | | | | |
| --- | --- | --- | --- | --- |
| Color | Channel | Myotome | Nerve | Spinal Level |
| Red | Right 1 | Right Abductor Pollicis Brevis | Median | C6, C7, C8, T1 |
| Orange | Right 2 | Right Vastus Medialis | Femoral | L2, L3, L4 |
| Yellow | Right 3 | Right Tibialis Anterior | Common Peroneal | L4, L5 |
| Green | Right 4 | Right Abductor Hallucis | Tibial | L4, L5, S1 |
| Blue | Left 1 | Left Abductor Pollicis Brevis | Median | C6, C7, C8, T1 |
| Violet | Left 2 | Left Vastus Medialis | Femoral | L2, L3, L4 |
| Gray | Left 3 | Left Tibialis Anterior | Common Peroneal | L4, L5 |
| White | Left 4 | Left Abductor Hallucis | Tibial | L4, L5, S1 |

TABLE 4

| Cervical | | | | |
| --- | --- | --- | --- | --- |
| Color | Channel | Myotome | Nerve | Spinal Level |
| Red | Right 1 | Right Deltoid | Axilliary | C5, C6 |
| Orange | Right 2 | Right Flexor Carpi Radialis | Median | C6, C7, C8 |
| Yellow | Right 3 | Right Abductor Pollicis Brevis | Median | C6, C7, C8, T1 |
| Green | Right 4 | Right Abductor Hallucis | Tibial | L4, L5, S1 |
| Blue | Left 1 | Left Deltoid | Axillary | C5, C6 |
| Violet | Left 2 | Left Flexor Carpi Radialis | Median | C6, C7, C8 |
| Gray | Left 3 | Left Abductor Pollicis Brevis | Median | C6, C7, C8, T1 |
| White | Left 4 | Left Abductor Hallucis | Tibial | L4, L5, S1 |

Figure 5:
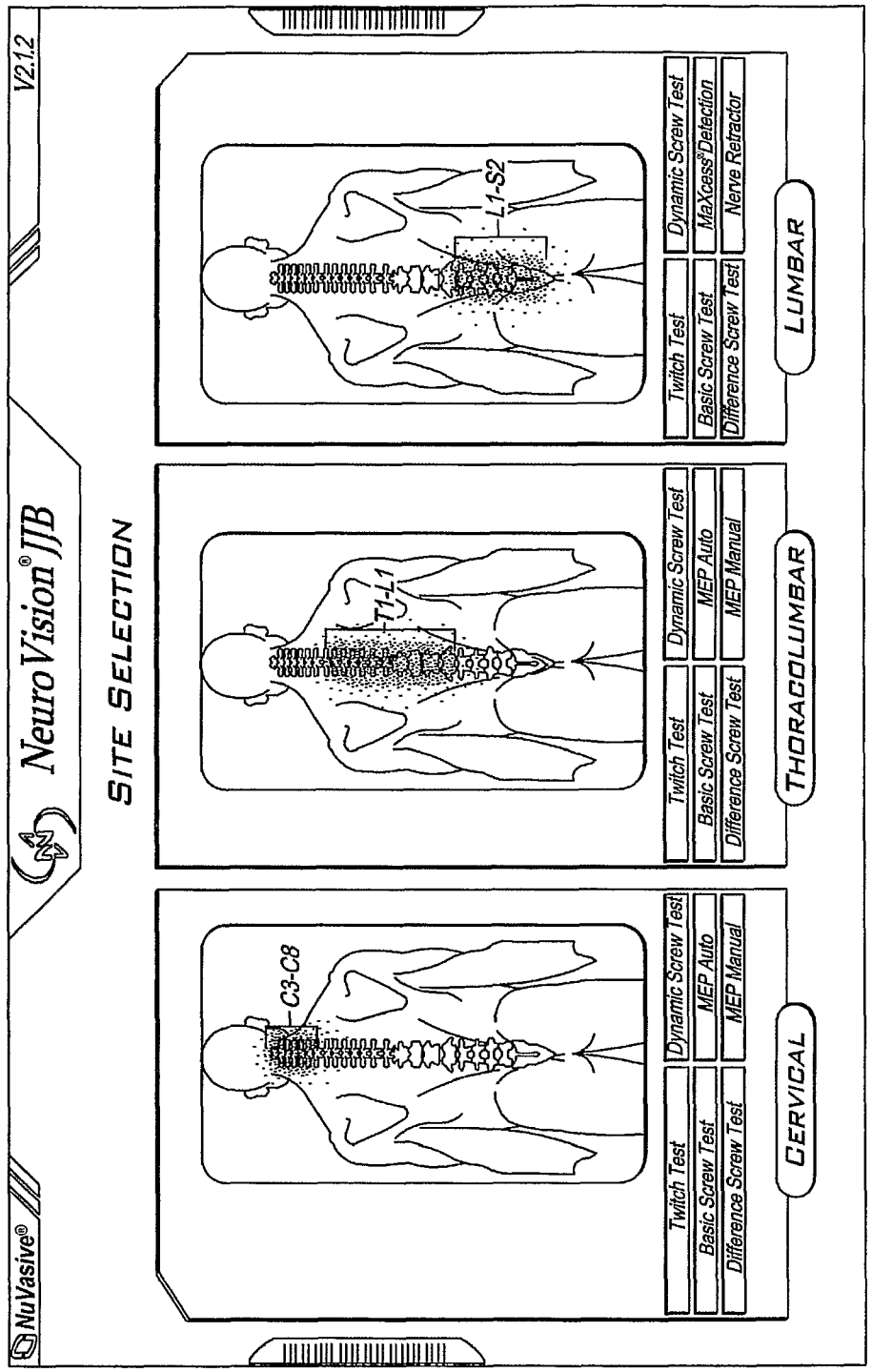
FIG. 5 is an illustration of an exemplary screen display for user selection of a spinal region to be monitored by the system of FIG. 3.

Various parameters and configurations of the neuromonitoring system 10 may depend upon the target location, i.e. spinal region, of the surgical procedure. In one embodiment, the user may select the location of the procedure from the GUI display 26 prior to selecting a desired function. A "site selection" screen is illustrated, by way of example only, in FIG. 5. Selecting a "site" preferably configures the system 10 to parameters designed for the selected region. By way of example, a default EMG configuration may be determined during site selection and EMG channels may be labeled with the corresponding myotome name and level, preferably, according to the configurations illustrated in Tables 2-4. In addition, the availability of different function modes may also depend upon the spinal region selected. By way of example only, selecting the cervical and thoracolumbar spinal regions may configure the options to allow selection of the Twitch Test, Basic Screw Test, Difference Screw Test, Dynamic Screw Test, MEP Auto, MEP Manual, and SSEP modes, while selecting the lumbar region may configure the options to allow selection of the Twitch Test, Basic Screw Test, Difference Screw Test, Dynamic Screw Test, MaXcess® Detection, and Nerve Retractor modes. Default parameters associated with the various function modes may also depend on the site selected; for example, the characteristics of the stimulation signal delivered by the system 10 may vary depending on the site selected. By way of example, the stimulation signal utilized for the screw test modes may be configured differently when the lumbar region is selected versus when one of the thoracic and cervical sites are selected (as described below).

Figure 7:
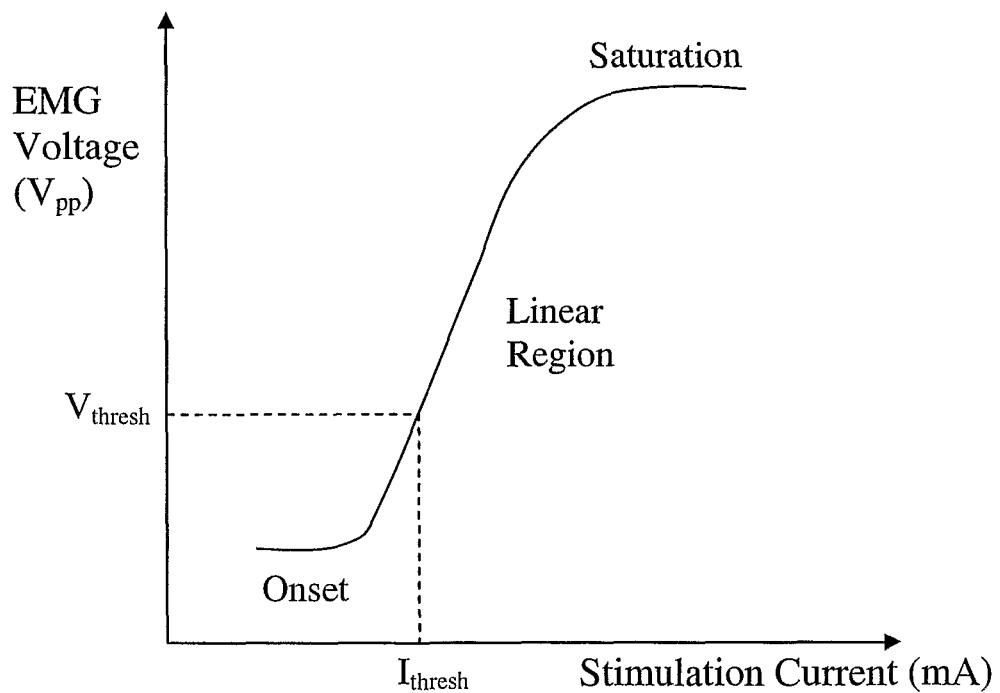
FIG. 7 is a graph illustrating a plot of peak-to-peak voltage (Vpp) for each given stimulation current level ($I_{Stim}$) forming a stimulation current pulse train according to the present invention (otherwise known as a "recruitment curve")

The neuromonitoring system 10 performs various functions (described below) by having the control unit 12 and patient module 14 (or MEP stimulator 21) cooperate to deliver stimulation signals to nearby nervous tissue and monitor muscle response to said stimulus. A basic premise underlying the methods employed by the system 10 for much of the neurophysiologic monitoring is that neurons and nerves have characteristic threshold current levels ($I_{Thresh}$) at which they will depolarize, resulting in detectable muscle activity. Below this threshold current, stimulation signals will not evoke a significant EMG response. Each EMG response can be characterized by a peak-to-peak voltage of $V_{pp}=V_{max}-V_{min}$, shown in FIG. 6. Once the stimulation threshold ($I_{Thresh}$) is reached, the evoked response is reproducible and increases with increasing stimulation until saturation is reached as shown in FIG. 7. This is known as a "recruitment curve." In one embodiment, a significant EMG response is defined as having a $V_{pp}$ of approximately 100 uV. The lowest stimulation signal current that evokes this threshold voltage ($V_{Thresh}$) is called $I_{Thresh}$. $I_{thresh}$ increases as the degree of electrical communication between a stimulation signal and a nerve decreases and conversely, $I_{thresh}$ decreases as the electrical communication increases between the nerve and stimulation signal. Thus monitoring $I_{thresh}$ can provide the surgeon with useful neurological information. By way of example, an excessively high $I_{thresh}$ or an increase over a previous measurement during MEP may indicate a problem in the spinal cord inhibiting transmission (communication) of the stimulation signal to the nerve. An excessively high $I_{thresh}$ or an increase over a previous measurement during nerve retractor mode may indicate a deterioration of nerve root function caused by over retraction. During Twitch Test mode $I_{thresh}$, may be utilized to determine the necessary current level to reliably conduct the test, thereby avoiding the need for excessive stimulation. During screw test and detection modes, a low $I_{thresh}$ value may indicate a breach in the pedicle allowing the electrical signal to escape the pedicle, or the close proximity of a nerve, respectively. Armed with the useful information conveyed by $I_{thresh}$, the surgeon may detect a problem or potential problem early and then act to avoid and/or mitigate the problem.

To obtain $I_{thresh}$ and take advantage of the useful information it provides, the system 10 identifies and measures the peak-to-peak voltage ($V_{pp}$) of each EMG response corresponding to a given stimulation current ($I_{stim}$). Identifying the true $V_{pp}$ of a response may be complicated by the existence of stimulation and/or noise artifacts which may create an erroneous $V_{pp}$ measurement. To overcome this challenge, the neuromonitoring system 10 of the present invention may employ any number of suitable artifact rejection techniques such as those shown and described in full in the above referenced co-pending and commonly assigned PCT App. Ser. No. PCT/US2004/025550, entitled "System and Methods for Performing Dynamic Pedicle Integrity Assessments," filed on Aug. 5, 2004. Upon measuring $V_{pp}$ for each EMG response, the $V_{pp}$ information is analyzed relative to the corresponding stimulation current ($I_{stim}$) in order to identify the minimum stimulation current ($I_{Thresh}$) capable of resulting in a predetermined $V_{pp}$ EMG response. According to the present invention, the determination of $I_{Thresh}$ may be accomplished via any of a variety of suitable algorithms or techniques.

FIGS. 8A-8D illustrate the fundamental steps of a threshold hunting algorithm used to quickly and accurately determine $I_{thresh}$. $I_{thresh}$ is, once again, the minimum stimulation current ($I_{stim}$) that results in an EMG response with a $V_{pp}$ greater than a predetermined threshold voltage, $V_{thresh}$. The basic method for finding $I_{thresh}$ utilizes a combination of a bracketing method and a bisection method. The bracketing method quickly finds a range (bracket) of stimulation currents that must contain $I_{thresh}$ and the bisection method narrows the bracket until $I_{thresh}$ is known within a specified accuracy. If $I_{thresh}$ on a given channel exceeds a predetermined maximum stimulation current, that threshold is considered out of range.

Figure 8A:
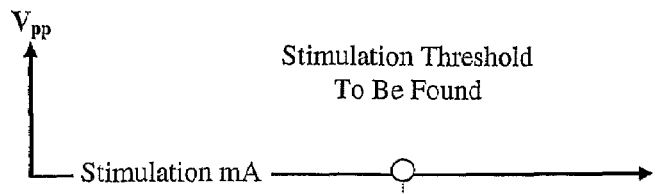
FIGS. 8A-8D are graphs illustrating the fundamental steps of a rapid current threshold-hunting algorithm according to one embodiment of the present invention.
Figure 8B:
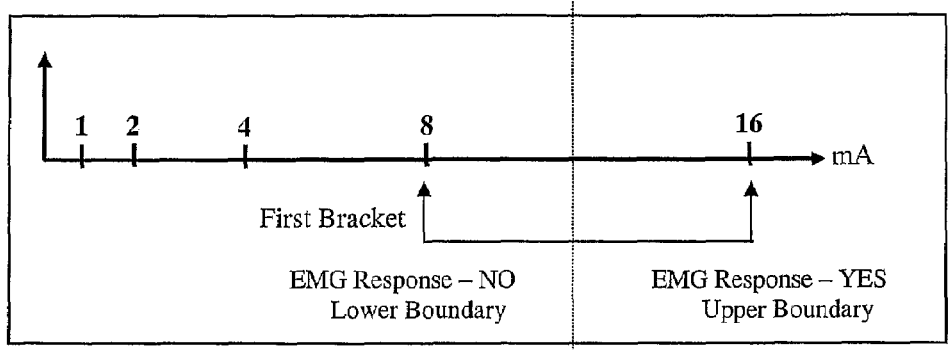

To find the initial bracket, the bracketing method adjusts the stimulation current as follows. Stimulation begins at a predetermined minimum stimulation current. The minimum stimulation current depends upon the selected function, by way of example only, the minimum stimulation current used for screw testing may be 1.0 mA while the minimum stimulation current used for MEP monitoring may be 60 mA. Each subsequent stimulation is delivered at a current level double that of the preceding current. This exponential doubling continues until a stimulation current results in an EMG response with a $V_{pp}$ greater than $V_{thresh}$ (i.e. it "recruits"). This first stimulation current to recruit, together with the last stimulation current to have not recruited, forms the initial bracket, as illustrated in FIG. 8B.

Figure 8C:
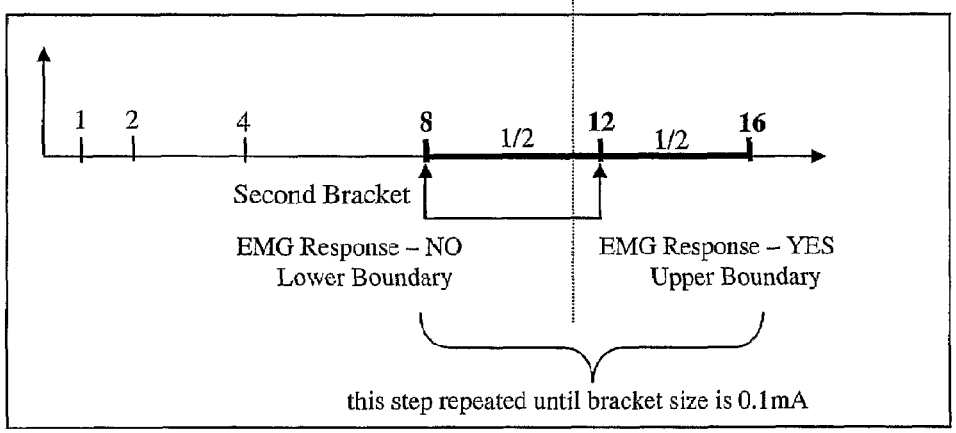
Figure 8D:
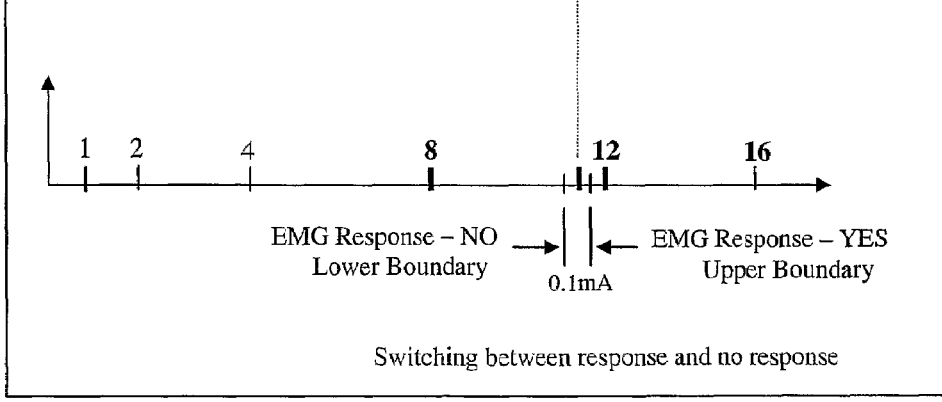

With respect to FIGS. 8C and 8D, after bracketing $I_{thresh}$, the bisection method is used as follows to reduce the bracket to a selected width, shown here by way of example only as 0.1 mA. Bracketing begins by stimulating with a current at the midpoint of the initial bracket. If the stimulation current recruits, the bracket shrinks to the lower half of the previous range. If the stimulation current does not recruit, the bracket shrinks to the upper half of the previous range. This process continues until $I_{thresh}$ is bracketed by stimulation currents separated by the selected width or resolution, 0.1 mA in this example. $I_{thresh}$ may be defined as any point falling within the final bracket such as for example, the midpoint of the bracket, the upper end of the bracket, and the lower end of the bracket. The bracketing and bisection steps may be repeated for all channels until $I_{thresh}$ is determined for each one.

Once the bracketing and bisection methods have been completed and $I_{thresh}$ found, a third method (confirmation phase) may be employed by the algorithm. During the confirmation phase, the algorithm may continuously check the validity of the original $I_{thresh}$ and ensure current thresholds are not changing. This may be accomplished, as illustrated in FIG. 8D, by switching back and forth between the upper and lower boundaries of the final bracket. If the threshold has not changed, then the lower end of the bracket should not evoke a response, while the upper end of the bracket should. If either of these conditions fail, the bracket is adjusted accordingly. The process may be repeated for each of the active channels to continue to assure that each threshold is bracketed. If stimulation signals fail to evoke the expected response three times in a row, then the algorithm transitions back to the bracketing state in order to reestablish the bracket.

During some functions (e.g. Screw Tests and Detection) stimulations may stop after $I_{thresh}$ is determined for the channel possessing the lowest $I_{thresh}$ For other functions (e.g. Nerve Retractor, MEP), however, it may useful to determine $I_{thresh}$ repeatedly for every channel. To accomplish this quickly, the hunting algorithm may employ additional methods allowing it to omit certain stimulations, thereby reducing the number of stimulations and time required to obtain an $I_{thresh}$ value on each channel. $I_{thresh}$ is still found using the bracketing and bisection methods described above, however the algorithm will omit stimulations for which the result is predictable from data previously acquired. When a stimulation signal is omitted, the algorithm proceeds as if the stimulation had taken place. This permits the algorithm to proceed to the next required stimulation immediately, without a time delay inherently associated with each stimulation signal. To further reduce the number of stimulations required over the time frame of an entire surgical procedure, the algorithm may confirm previously obtained $I_{thresh}$ values (e.g. by stimulation at current levels just below and/or just above $I_{thresh}$ and determining whether the resulting responses are consistent with the previously acquired $I_{thresh}$ value), rather than initiating stimulations from the beginning each time a function is performed.

Although the hunting algorithm is discussed herein in terms of finding $I_{thresh}$ (the lowest stimulation current that evokes a predetermined EMG response), it is contemplated that alternative stimulation thresholds may be useful in assessing the health of the spinal cord or nerve monitoring functions and may be determined by the hunting algorithm. By way of example only, the hunting algorithm may be employed by the system 10 to determine a stimulation voltage threshold, $Vstim_{thresh}$. This is the lowest stimulation voltage (as opposed to the lowest stimulation current) necessary to evoke a significant EMG response, $V_{thresh}$. Bracketing, bisection and monitoring states are conducted as described above for each active channel, with brackets based on voltage being substituted for the current based brackets previously described.

The neuromonitoring system 10 may test the integrity of pedicle holes during all aspects of pilot hole formation (e.g., via an awl), pilot hole preparation (e.g. via a tap), and screw introduction (before, during, and after) via the Basic Screw Test, Difference Screw Test, and/or Dynamic Screw Test modes. These modes are described in detail in Int'l Patent App. No. PCT/US02/35047 entitled "System and Methods for Performing Percutaneous Pedicle Integrity Assessments," filed on Oct. 30, 2002, and PCT/US2004/025550, entitled "System and Methods for Performing Dynamic Pedicle Integrity Assessments," filed on Aug. 5, 2004 the entire contents of which are both hereby incorporated by reference as if set forth fully herein. In general, the Basic Screw Test, Difference Screw Test, and Dynamic Screw Test modes are designed to assess the integrity of bone by monitoring the degree of electrical communication between the hole formation/preparation tool and/or screw and the nearby nerve tissue via stimulation threshold determination, preferably using the hunting algorithm described above.

As mentioned above, each of the screw test modes may be performed in the lumbar thoracic, and cervical spines. While the basic principle of the screw test remains the same for all levels (i.e. monitoring communication between instrument/screw and nerve tissue via $I_{thresh}$ monitoring), certain distinctions may apply depending on the level selected. Because of the proximity of the spinal cord to thoracic and cervical pedicles, for example, the stimulation signal characteristics used for lumbar testing may not be effective when monitoring in the thoracic and/or cervical levels. To account for this, the surgical system 10 is equipped to deliver stimulation signals having different characteristics based on the region selected. By way of example only, when the lumbar region is selected stimulation signals for the screw test modes comprise single pulse signals. On the other hand, when the thoracic and cervical regions are selected the stimulation signals may be configured as multipulse signals.

Figure 9:
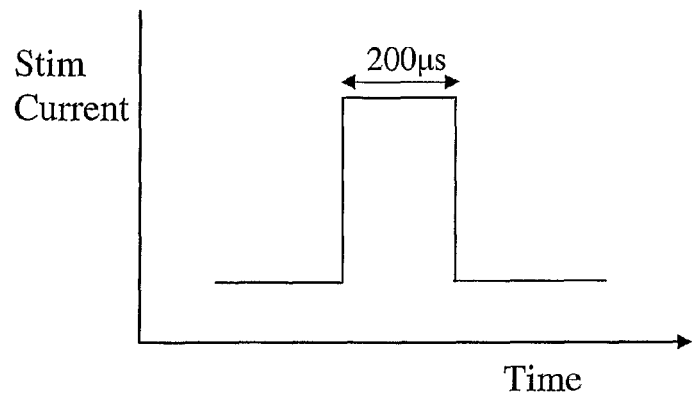
FIG. 9 is a graph illustrating an exemplary single pulse stimulation signal according to one embodiment of the present invention.

A single pulse signal such as is preferably utilized for the Basic, Difference, and Dynamic screw tests is illustrated by way of example only in FIG. 9. The single pulse stimulation signal comprises a single monophasic pulse of 200 µs duration with the amplitude of the pulse being automatically adjusted according to the threshold hunting algorithm. The control unit 12 associates a single neuromuscular response, or lack thereof, with each stimulation signal delivered; thus the ratio of electrical pulses delivered versus responses recorded is 1/1.

Figure 10:
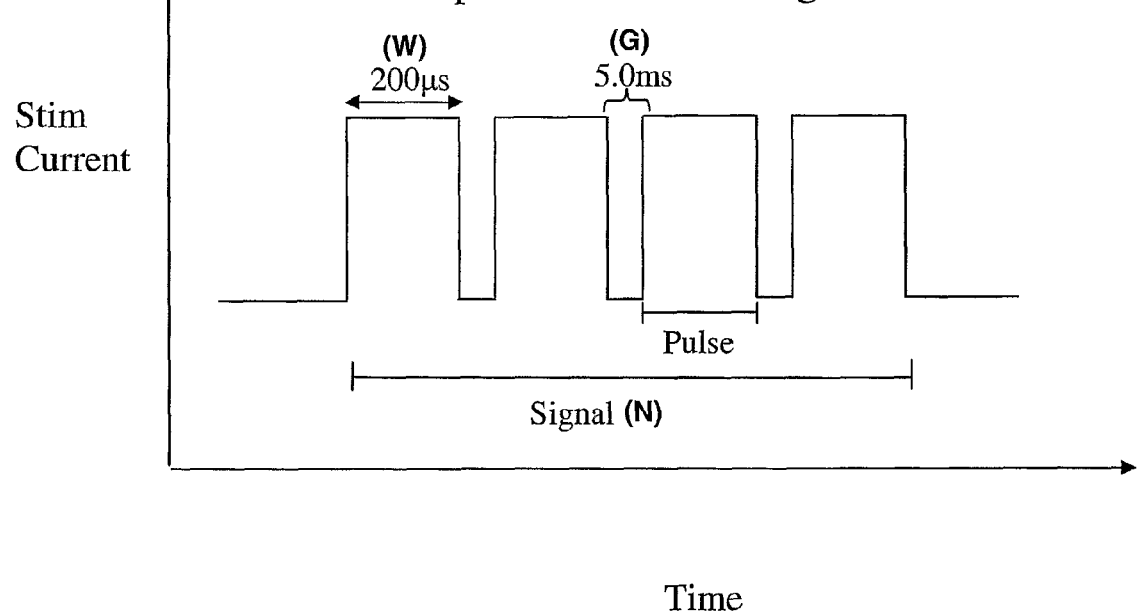
FIG. 10 is a is a graph illustrating an exemplary multipulse stimulation signal according to one embodiment of the present invention.

To achieve reproducible results when stimulating the spinal cord (as occurs when detecting a medial breach in thoracic and cervical pedicles), the neuromonitoring system 10 utilizes a multipulse stimulation signal when employing the Basic, Difference, and Dynamic screw test modes in the thoracic or cervical spine. FIG. 10 illustrates, by way of example only, a multipulse stimulation signal used for thoracic and cervical screw tests. The multipulse stimulation signal comprises several stimulation pulses of a constant current grouped together as one single stimulation signal. By way of example, multipulse stimulation signals may include a train of pulses (N) ranging in number from 2 to 8. Pulses may be separated by an interpulse gap (G) ranging from 1 ms to 10 ms and pulse widths (W) may range from 50 µs to 400 µs. An exemplary configuration of the multipulse signal may include 4 monophasic pulses (N) of 200 µs (W), separated by an interpulse gap of 5 ms (G). Each multipulse signal is associated with a single neuromuscular response, or lack thereof; thus the ratio of electrical pulses delivered versus responses recorded will be greater than 1/1. Activating the spinal cord with a single stimulation current is less reproducible than activating a nerve root. The use of the multipulse stimulation signal may improve that reproducibility and result in a more reliable stimulation threshold determination for the spinal cord.

Default stimulation signal characteristics are assigned by the system 10 based upon spine region selected during site selection, as described above. The final decision whether to proceed with a single pulse signal or multipulse signal, as well as the specific parameters of each signal, lies with the responsible clinician or surgeon and should be based on their experience and needs. The parameters of the stimulation signal may be adjusted as desired at any time. This may preferably be accomplished using either a standard setup screen or a function specific setup screen (not shown) on the GUI display.

With reference to FIG. 3, a screw test probe 34 is provided for performing pedicle integrity tests. Screw test probe includes a handle, preferably the stimulation handle 40, and a probe member 36 having a generally ball-tipped end 38. The screw test handle 40 may be equipped with one or more buttons 41 for selectively applying electrical stimulation to the ball-tipped end 38 at the end of the probe member 36. In one embodiment, the probe member 36 is disposable and the handle 40 is reusable and autoclavable.

Also with reference to FIG. 3, an electric coupling device 42 may be utilized to couple a surgical tool, such as for example, a tap member 72 or a bone awl 74, to the surgical system 10. In this manner, a stimulation signal may be passed through the surgical tool and screw testing can be performed while the tool is in use. The electric coupling device 42 may comprise a number of possible embodiments that permit the device to attach and hold a surgical tool while allowing transmission of a stimulation signal to the tool. One such electric coupling device 42 utilizes a spring-loaded plunger to hold the surgical tool and transmit the stimulation signal. The plunger rod 44 is composed of a conductive material such as metal. A nonconductive housing 46 partially encases the rod 44 about its center. Extending from the housing 46 is an end plate 48. An electrical cable 50 connects the electric coupling device 42 to the handle 40. A spring (not shown) is disposed within the housing 46 such that in a natural or "closed" state the plunger 44 is situated in close proximity to the endplate 48. Exerting a compressive force on the spring (such as by pulling the cable 50 while holding the housing 46) causes a gap between the end plate 48 and the plunger 44 to widen to an "open" position, thereby allowing insertion of a surgical tool between the end plate 48 and plunger 44. Releasing the cable 50 allows the spring to return to a "closed" position, causing the plunger 44 to move laterally back towards the endplate such that a force is exerted upon the surgical tool and thereby holds it in place between the endplate 48 and the plunger 44. Thereafter the electrical stimulus may be passed from the handle 40 through the cable 50 and plunger 44 to the surgical tool.

Alternatively, the electrical coupling device may be embodied in the form of a clip 52. The clip 52 is comprised of two prongs hingedly coupled at a coupling point 54 such that the clip 52 includes an attachment end 56 and a non-attachment end 58. A stimulation electrode 60 is disposed on the attachment end 56 and communicates with an electric cable 50 extending from the non-attachment end 58 to the handle 34. In a "closed" position the prong ends at the attachment end 56 touch. Depressing the prongs at the non-attachment end 58 in a direction towards each other causes a gap to form between the prong ends at the attachment end 56. Positioning the "opened" attachment end 56 over a desired surgical tool and releasing the force on the non-attachment end 58 causes the attachment end 56 to pinch tight on the surgical tool and thereby allow the electrical stimulus to pass from the screw test handle 34, through the stimulation electrode 60, to the surgical tool.

To perform the Basic Screw Test the screw test probe 34 is placed in the screw hole prior to screw insertion or placed on the installed screw head stimulation is activated from one or more buttons on the stimulation handle 40 or from the GUI display 26. As previously discussed the parameters of the stimulation signal vary depending upon which region of the spine is selected. Stimulations will commence according to the algorithm described above and continue until $I_{thresh}$ is determined. In one embodiment the algorithm ceases after the lowest $I_{thresh}$ is determined. Alternatively, the algorithm may continue until $I_{thresh}$ is found for every channel, omitting stimulations as described above when applicable. The insulating character of bone will prevent the stimulation current, up to a certain amplitude, from communicating with the nerve, thus resulting in a relatively high $I_{thresh}$, as determined via the basic threshold hunting algorithm described above. However, in the event the pedicle wall has been breached by the screw or tap the current density in the breach area will increase to the point that the stimulation current will pass through to the adjacent neural tissue and it will depolarize at a lower stimulation current, thus $I_{thresh}$ will be relatively low. If a breach or potential breach is detected, the user may simply redirect the pilot hole formation or withdraw the misplaced pedicle screw and redirect to ensure proper placement.

The Difference Screw Test is similar to the Basic Screw Test; however, a baseline threshold value is determined by directly stimulating a nerve with probe 34. After establishing the baseline threshold the screw or pilot hole is stimulated according to the algorithm and the threshold result is compared to the baseline result. The difference value may then be used indicate the relative safety level.

In Dynamic Screw Test mode, electric coupling device 42 or 52 may be utilized to couple a surgical tool, such as for example, a tap member 72 or a bone awl 74, to the neuromonitoring system 10. In this manner, stimulation signals may be passed through the surgical tool and pedicle integrity testing can be performed while the tool is in use. Thus, screw testing may be performed during pilot hole formation by coupling the bone awl 74 to the neuromonitoring system 10 and during pilot hole preparation by coupling the tap 72 to the system 10. Likewise, by coupling a pedicle screw to the neuromonitoring system 10 (such as via pedicle screw instrumentation), screw testing may be performed during screw introduction. Upon activating the dynamic screw test, stimulations are delivered according to the algorithm until $I_{thresh}$ is found. Unlike the Basic and Difference tests, the Dynamic screw test continually monitors and updates $I_{thresh}$ until the user stops the test. To do so, the algorithm preferably uses the confirmation step described above to quickly and continuously update the threshold results.

Figure 11:
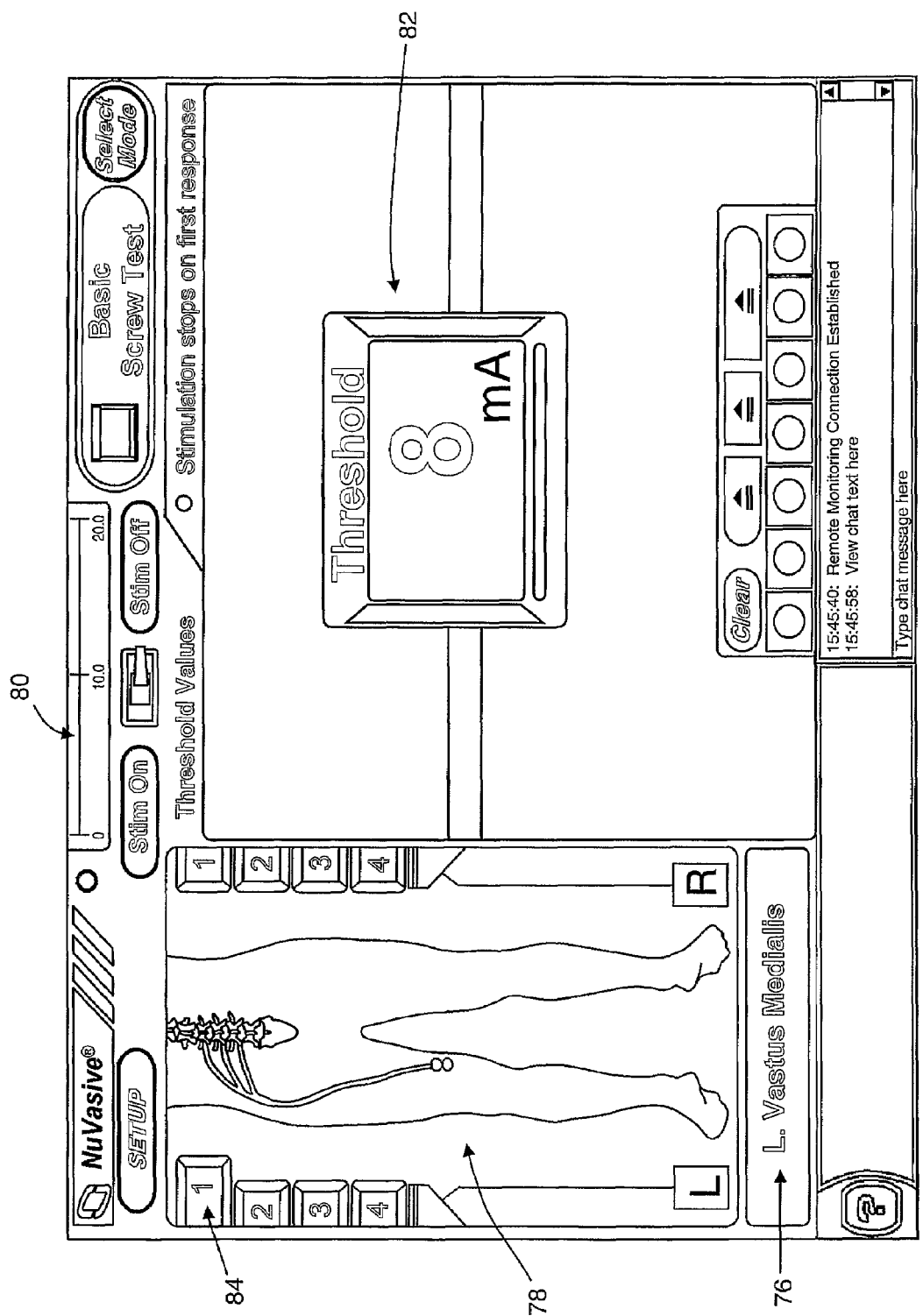
FIG. 11 is an exemplary screen display illustrating one embodiment of the Basic Screw Test mode for performing pedicle integrity assessments with according to the present invention.
Figure 12:
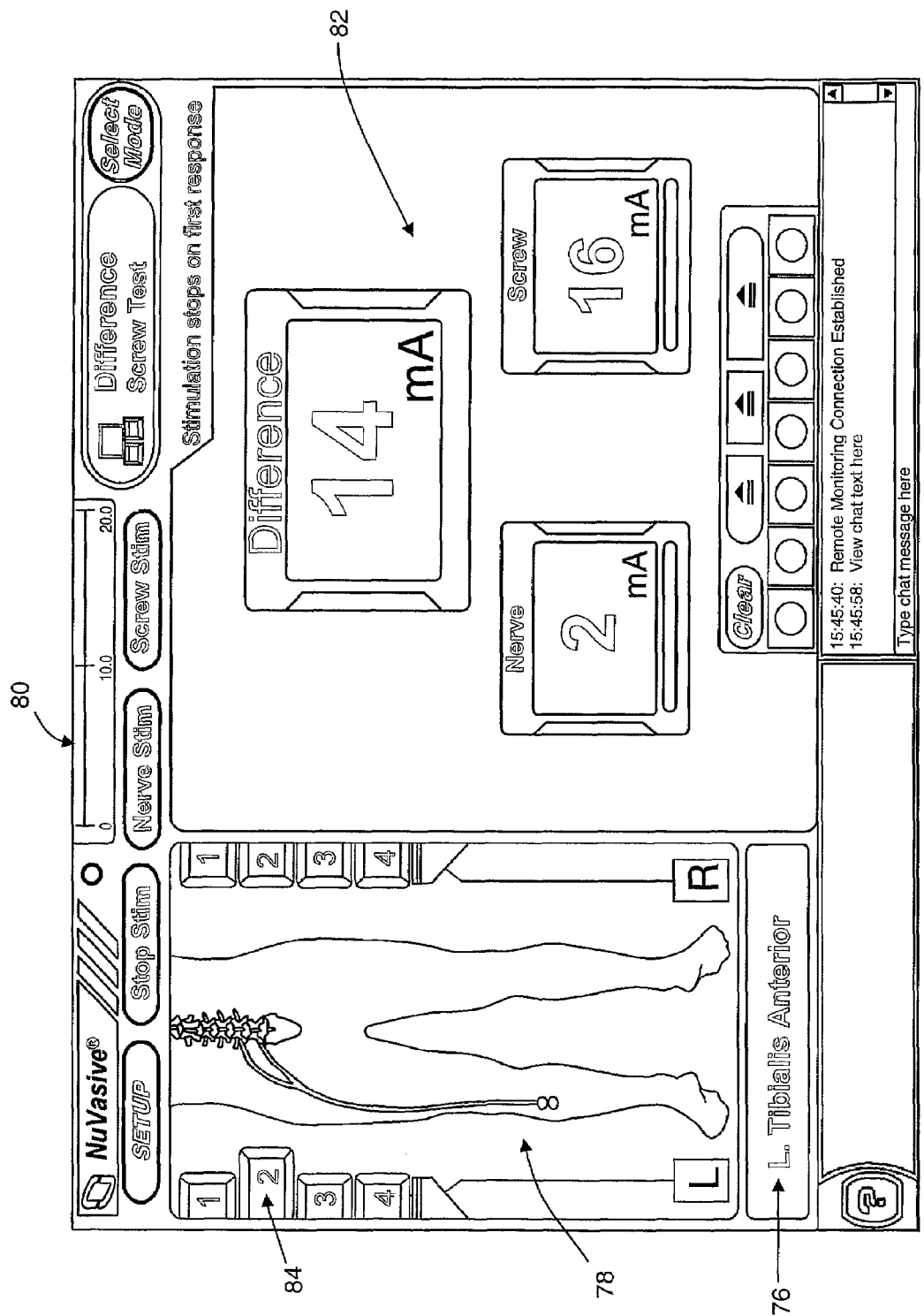
FIG. 12 is an exemplary screen display illustrating one embodiment of the Difference Screw Test mode for performing pedicle integrity assessments according to the present invention.
Figure 13:
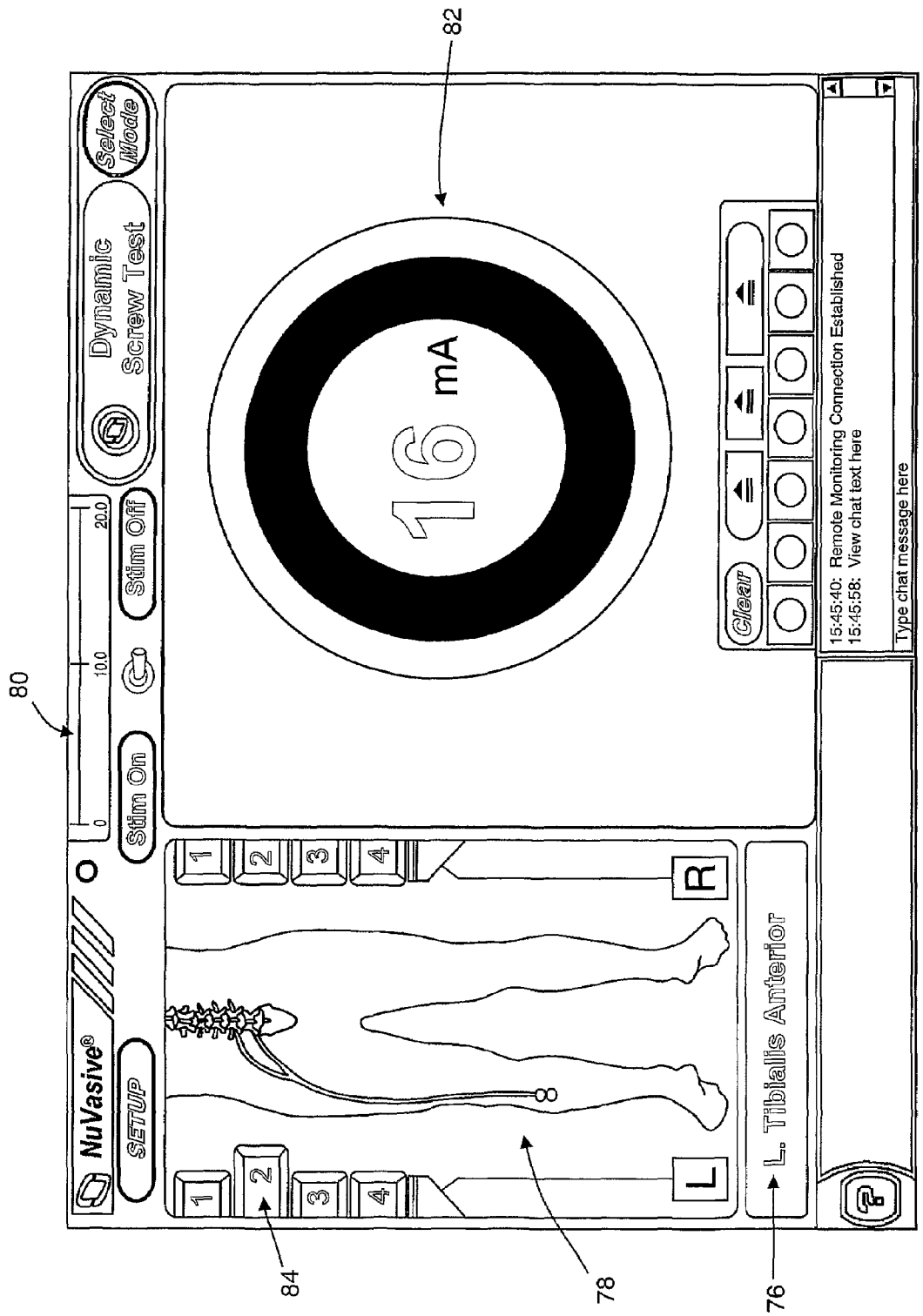
FIG. 13 is an exemplary screen display illustrating one embodiment of the Dynamic Screw Test mode for performing pedicle integrity assessments according to the present invention.

Stimulation results and other relevant data are conveyed to the user on display 26, as illustrated in FIGS. 11-13. FIG. 11 is an exemplary screen view of the Basic Screw Test mode. FIG. 12 illustrates an exemplary screen view of the Difference Screw Test mode. FIG. 13 is an exemplary screen view of the Dynamic Screw Test mode. Upon execution of the algorithm, one or more channel tabs may be highlighted using a color-code to indicate status of the corresponding nerve, and thus the relative safety level determined by the system 10. The channel with the "worst" (lowest) level will preferably be enlarged and that myotome name 76 will be displayed, as well as graphically depicted on the spine diagram 78. A vertical bar chart 80 may also be shown to depict the stimulation current required to evoke a significant response for the selected channel. A large numerical readout 82 may also indicate the value of the stimulation result. Preferably, the display of the stimulation result may be augmented with a color code utilizing the colors green, yellow, and red to enhance the understandability of the result and quickly indicate to the surgeon the level of safety determined by the system 10. Red may be used to indicate an $I_{thresh}$ level below a predetermined unsafe level. Yellow may be used to indicate an $I_{thresh}$ that falls in between predetermined safe and unsafe levels. Green may represent an $I_{thresh}$ within the range predetermined as safe. Although not show, the threshold results may be replaced with, or more preferably, augmented with a display of the actual waveform for each channel, as well as audible sounds distinctive to each level of safety (safe, unsafe, in between).

Other functional modes of the neuromonitoring system 10 may include, but are not necessarily limited to, the Twitch Test, Free-run EMG, MaXcess® Detection, Nerve Retractor, MEP Auto, MEP manual, and SSEP modes. The Twitch Test mode is designed to assess the neuromuscular pathway via the so-called "train-of-four test" test to ensure the neuromuscular pathway is free from muscle relaxants prior to performing neurophysiology-based testing, such as screw testing, nerve detection, and nerve retraction. This is described in greater detail within Int'l Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The MaXcess® Detection mode is designed to detect the presence of nerves during the use of the various surgical access instruments of the neuromonitoring system 10, including the k-wire 62, dilator 64, cannula 66, retractor assembly 68. This mode is described in greater detail within Int'l Patent App. No PCT/US02/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within Int'l Patent App. No. PCT/US02/30617, entitled "System and Methods for Performing Surgical Procedures and Assessments," filed on Sep. 25, 2002, the entire contents of which is hereby incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. The SSEP function is designed to test the sensory pathway to detect potential damage to the spinal cord by stimulating peripheral nerves inferior to the target spinal level and recording the action potential from sensors superior to the spinal level. The MEP Auto, MEP manual, and SSEP modes are described in greater detail within Int'l Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein. These functions will be explained now in brief detail.

The neuromonitoring system 10 performs neuromuscular pathway (NMP) assessments, via Twitch Test mode, by electrically stimulating a peripheral nerve via PNS electrodes 24 placed on the skin over the nerve or by direct stimulation of a spinal nerve using a surgical accessory such as screw test probe 34. Evoked responses from the muscles innervated by the stimulated nerve are detected and recorded, the results of which are analyzed and a relationship between at least two responses or a stimulation signal and a response is identified. The identified relationship provides an indication of the current state of the NMP. The identified relationship may include, but is not necessarily limited to, one or more of magnitude ratios between multiple evoked responses and the presence or absence of an evoked response relative to a given stimulation signal or signals.

The neuromonitoring system 10 may perform nerve proximity testing, via the MaXcess® Detection mode, to ensure safe and reproducible access to surgical target sites. Using the surgical access components 62-66, the system 10 detects the existence of neural structures before, during, and after the establishment of an operative corridor through (or near) any of a variety of tissues having such neural structures which, if contacted or impinged, may otherwise result in neural impairment for the patient. The surgical access components 62-66 are designed to bluntly dissect the tissue between the patient's skin and the surgical target site. Cannulae or dilators of increasing diameter, which are equipped with one or more stimulating electrodes, are advanced towards the target site until a sufficient operating corridor is established. As the cannulae or dilators are advanced to the target site electrical stimulation signals are emitted via the stimulation electrodes. The stimulation signal will stimulate nerves in close proximity to the stimulation electrode and the corresponding EMG response is monitored. As a nerve gets closer to the stimulation electrode, the stimulation current ($I_{stim}$) required to evoke a muscle response decreases. $I_{thresh}$ is calculated, using the basic threshold hunting algorithm described above, providing a measure of the communication between the stimulation signal and the nerve and thus giving a relative indication of the proximity between access components and nerves.

Additional and/or alternative surgical access components such as, by way of example only, a tissue retraction assembly 68 (FIG. 3) may be coupled to the system 10 and employed to provide safe and reproducible access to a surgical target site. Tissue retraction assembly 68 and various embodiments and uses thereof have been shown and described co-pending and commonly assigned U.S. patent application Ser. No. 10/967,668, entitled "Surgical Access System and Related Methods," filed on Oct. 18, 2004, the entire contents of which are expressly incorporated by reference as if set forth herein in their entirety.

The neuromonitoring system 10 preferably accomplishes neural pathology monitoring via the Nerve Retractor mode, specifically by determining a baseline stimulation threshold with direct contact between the nerve retractor 70 and the nerve, prior to retraction. Subsequent stimulation thresholds are determined during retraction and they are compared to the baseline threshold. Significant changes in the stimulation threshold may indicate potential trauma to the nerve caused by the retraction and are displayed to the user on the display 26. An increase in $I_{thresh}$ over time is an indication that the nerve function is deteriorating and retraction should be reduced or stopped altogether to prevent permanent damage. $I_{thresh}$ is preferably determined for each channel according to the multi-channel hunting algorithm described above.

The neuromonitoring system 10 performs assessments of spinal cord health using one or more of MEP Auto, MEP Manual, and SSEP modes. In MEP modes, stimulation signals are delivered to the Motor Cortex via MEP stimulator 22 and resulting EMG responses are detected from various muscles in the upper and lower extremities. An increase in $I_{thresh}$ from an earlier test to a later test may indicate a degradation of spinal cord function. Likewise, the absence of a significant EMG response to a given $I_{stim}$ on a channel that had previously reported a significant response to the same or lesser $I_{stim}$ is also indicative of a degradation in spinal cord function. These indicators are detected by the system in the MEP modes and reported to the surgeon. In MEP Auto mode, the system determines the $I_{thresh}$ baseline for each channel corresponding to the various monitored muscles, preferably early in the procedure, using the multi-channel algorithm described. Throughout the procedure, subsequent tests may be conducted to again determine $I_{thresh}$ for each channel. The difference between the resulting $I_{thresh}$ values and the corresponding baseline are computed by the system 10 and compared against predetermined "safe" and "unsafe" difference values. The $I_{thresh}$, baseline, and difference values are displayed to the user, along with any other indicia of the safety level determined (such as a red, yellow, green color code). In MEP Manual mode, the user selects the stimulation current level and the system reports whether or not the stimulation signal evokes a significant response on each channel. Stimulation results may be represented as "YES" and "NO" responses, or other equivalent indicia. Using either mode, the surgeon may thus be alerted to potential complications with the spinal cord and any corrective actions deemed necessary may be undertaken at the discretion of the surgeon.

In SSEP mode, the neuromonitoring system 10 stimulates peripheral sensory nerves that exit the spinal cord below the level of surgery and then measures the electrical action potential from electrodes located on the nervous system tract superior to the surgical target site. To accomplish this, peripheral nerve stimulation (PNS) electrodes 24 may be placed on the skin over the desired peripheral nerve (such as by way of example only, the Posterior Tibial nerve) and recording electrodes 41 are positioned on the recording site (such as, by way of example only, the skin over the C2 vertebra) and stimulation signals are delivered from the patient module 14. Damage in the spinal cord may disrupt the transmission of the signal up the cord resulting in a weakened or delayed signal at the recording site. The system 10 determines differences in amplitude and latency between a signal response and a baseline signal response. The differences are compared against predetermined "safe" and "unsafe" levels.

The neuromonitoring system 10 may also conduct free-run EMG monitoring while the system is in any of the above-described modes. Free-run EMG monitoring continuously listens for spontaneous muscle activity that may be indicative of potential danger. The system 10 may automatically cycle into free-run monitoring after 5 seconds (by way of example only) of inactivity. Initiating a stimulation signal in the selected mode will interrupt the free-run monitoring until the system 10 has again been inactive for five seconds at which time the free-run begins again.

While this invention has been described in terms of a best mode for achieving this invention's objectives, it will be appreciated by those skilled in the art that variations may be accomplished in view of these teachings without deviating from the spirit or scope of the present invention. By way of example the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A method for testing the integrity of bone in one of the thoracic and cervical regions of the spine, comprising the steps of:
    transmitting a series of stimulation signals from a surgical instrument to nervous tissue proximate to one of a thoracic and cervical vertebra pedicle, each stimulation signal in said series of stimulation signals comprising at least two electrical pulses;
    sensing from at least one sensor a neuromuscular response associated with each stimulation signal in said series of stimulation signals, wherein the ratio between said pulses and said neuromuscular response is greater than a one-to-one ratio; and
    assessing whether the pedicle is one of breached and is close to breached due to one of screw placement, hole formation, and hole preparation into said pedicle.

2. The method of claim 1, wherein transmitting a series of stimulation signals includes coupling the surgical instrument to a signal generator.

3. The method of claim 1, wherein the sensor and the surgical instrument are in communication with a control unit and the control unit (a) directs transmission of the stimulation signals, (b) receives and processes neuromuscular response data sensed by the sensor, and (c) identifies a relationship between the stimulation signal and the neuromuscular response to assess whether the pedicle is one of breached and nearly breached.

4. The method of claim 3, wherein the identified relationship is the threshold stimulation current required to achieve a neuromuscular response of a predetermined magnitude.

5. The method of claim 4, wherein the control unit determines the threshold stimulation current once and stops.

6. The method of claim 4, wherein the control unit determines the threshold stimulation current repeatedly until stopped by user intervention.

7. The method of claim 3, wherein the control unit includes a display and comprising the further step of displaying at least one of graphical, alpha-numeric, and color based indicia to communicate the identified relationship between the stimulation signal and the neuromuscular response.

8. The method of claim 7, wherein the display includes a graphical user interface configured to receive user instructions and comprising the further step of operating the graphical user interface to direct the control unit in one or more of selecting a target spinal region, initiating stimulation, ending stimulation, and altering parameters utilized by the control unit.

9. The method of claim 1, wherein said stimulation signal comprises between 2 and 8 pulses having pulse widths of between 50 μs and 400 μs and separated by interpulse delays of between 1 ms and 10 ms.

10. The method of claim 1, wherein the surgical instrument is a screw test probe and further comprising the step of placing the screw test probe one of within a hole formed in the pedicle and in contact with a screw implanted within the hole prior to transmitting the stimulation signal.

11. The method of claim 1, wherein the surgical instrument is a standard operating tool linked to the control unit with a coupling device.

12. The method of claim 3, comprising the further step of repeating steps (a)-(c) while one of forming and preparing a hole within the pedicle with the surgical instrument.

13. The method of claim 4, comprising the further step of executing an algorithm that automatically controls the amplitude of the stimulation signal to identify the threshold stimulation current.

14. The method of claim 4, comprising the further step of establishing a bracket that contains the threshold stimulation current to identify the threshold.

15. The method of claim 4, comprising the further step of bisecting a bracket that contains the threshold stimulation current to identify the threshold.

16. The method of claim 4, comprising the further steps of continuously verifying a stimulation threshold result by repeatedly stimulating back and forth at the upper end and lower end of a bracket of predetermined width which contains the stimulation current threshold.

17. The method of claim 16, comprising the further step of establishing a new bracket if the threshold result cannot be verified.

18. The method of claim 1, wherein the at least one sensor is an electromyography electrode and comprising the further step of measuring the voltage associated with the neuromuscular response.

19. The method of claim 18, wherein the one or more electromyography electrodes comprises 8 EMG sensors.

20. A method for testing the integrity of bone in one of the thoracic and cervical regions of the spine, comprising the steps of:
    transmitting a series of stimulation signals from a surgical instrument to nervous tissue proximate to one of a thoracic and cervical vertebra pedicle; each stimulation signal in said series of stimulation signals comprising multiple electrical pulses of equal current, equal duration, and equal interpulse delays;
    sensing from at least one sensor a neuromuscular response associated with each stimulation signal in said series of stimulation signals wherein the ratio between said multiple electrical pulses and said neuromuscular response is greater than a one-to-one ratio; and assessing whether the pedicle is one of breached and is close to breached due to one of screw placement, hole formation, and hole preparation into said pedicle.

21. The method of claim 20, wherein the sensor and the surgical instrument are in communication with a control unit and the control unit (a) directs transmission of the stimulation signal, (b) receives and processes neuromuscular response data sensed by the sensor, and (c) identifies a relationship between the stimulation signal and the neuromuscular response to assess whether the pedicle is one of breached and nearly breached.

22. The method of claim 21, wherein the identified relationship is the threshold stimulation current required to achieve a neuromuscular response of a predetermined magnitude.

23. The method of claim 20, wherein the control unit includes a display, said display includes a graphical user interface configured to receive user instructions and comprising the further step of operating the graphical user interface to direct the control unit in one or more of selecting a target spinal region, initiating stimulation, ending stimulation, and altering parameters utilized by the control unit, and comprising the further step of displaying at least one of graphical, alpha-numeric, and color based indicia to communicate the identified relationship between the stimulation signal and the neuromuscular response.

24. The method of claim 20, wherein said stimulation signal comprises between 2 and 8 pulses having pulse widths of between 50 μs and 400 μs and separated by interpulse delays of between 1 ms and 10 ms.

25. The method of claim 20, wherein the surgical instrument is a screw test probe and further comprising the step of placing the screw test probe one of within a hole formed in the pedicle and in contact with a screw implanted within the hole prior to transmitting the stimulation signal.

* * * * *